US007998500B2

(12) United States Patent
Squashic et al.

(10) Patent No.: US 7,998,500 B2
(45) Date of Patent: Aug. 16, 2011

(54) NUTRITIONAL SUPPLEMENT FOR WOMEN

(75) Inventors: Steven A. Squashic, Scotch Plains, NJ (US); Kevin M. Hudy, Hoboken, NJ (US); David C. Purdy, Tinton Falls, NJ (US)

(73) Assignee: Vertical Pharmaceuticals, Inc., Sayreville, NJ (US)

( * ) Notice: Subject to any disclaimer, the term of this patent is extended or adjusted under 35 U.S.C. 154(b) by 803 days.

(21) Appl. No.: 11/197,760

(22) Filed: Aug. 4, 2005

(65) Prior Publication Data

US 2007/0031487 A1    Feb. 8, 2007

(51) Int. Cl.
  *A61K 9/20* (2006.01)
  *A61K 9/48* (2006.01)
  *A61K 9/28* (2006.01)
  *A61K 47/10* (2006.01)

(52) U.S. Cl. ........ 424/439; 424/464; 424/451; 424/466; 424/474; 514/52; 514/351; 514/904; 514/905

(58) Field of Classification Search .................. 424/451, 424/464, 630, 641, 643, 646, 439; 514/52, 514/167, 249, 251, 276, 351, 355, 458, 474, 514/566, 567, 725, 904, 905
See application file for complete search history.

(56) References Cited

U.S. PATENT DOCUMENTS

| | | | |
|---|---|---|---|
| 3,258,846 A | 7/1966 | Powell, Jr. | |
| 4,582,709 A | 4/1986 | Peters et al. | |
| 4,629,625 A * | 12/1986 | Gaull | 424/643 |
| 4,752,479 A | 6/1988 | Briggs et al. | |
| 4,786,510 A | 11/1988 | Nakel et al. | |
| 4,786,518 A | 11/1988 | Nakel et al. | |
| 4,812,303 A | 3/1989 | Iorio | |
| 4,867,989 A | 9/1989 | Silva et al. | |
| 4,973,467 A | 11/1990 | Sahley | |
| 4,980,168 A | 12/1990 | Sahley | |
| 4,992,282 A | 2/1991 | Mehansho et al. | |
| 4,994,283 A | 2/1991 | Mehansho et al. | |
| 5,021,424 A | 6/1991 | Lawton-Wall | |
| 5,051,258 A | 9/1991 | Sahley | |
| 5,061,723 A | 10/1991 | Barua et al. | |
| 5,151,274 A | 9/1992 | Saltman et al. | |
| 5,223,285 A | 6/1993 | DeMichele et al. | |
| 5,308,627 A | 5/1994 | Umbdenstock, Jr. | |
| 5,312,626 A | 5/1994 | Gergely et al. | |
| 5,332,579 A | 7/1994 | Umbdenstock | |
| 5,445,837 A | 8/1995 | Burkes et al. | |
| 5,447,732 A | 9/1995 | Tanimoto et al. | |
| 5,468,506 A | 11/1995 | Andon | |
| 5,494,678 A | 2/1996 | Paradissis et al. | |
| 5,496,567 A | 3/1996 | McLean | |
| 5,501,857 A | 3/1996 | Zimmer | |
| 5,514,382 A | 5/1996 | Sultenfuss | |
| 5,562,869 A | 10/1996 | Drahos et al. | |
| 5,569,458 A | 10/1996 | Greenberg | |
| 5,569,459 A | 10/1996 | Shlyankevich | |
| 5,569,477 A | 10/1996 | Nesbitt | |
| 5,571,441 A | 11/1996 | Andon et al. | |
| 5,597,585 A | 1/1997 | Williams et al. | |
| 5,612,061 A | 3/1997 | Rabkin | |
| 5,614,553 A | 3/1997 | Ashmead et al. | |
| 5,626,883 A | 5/1997 | Paul | |
| 5,646,116 A | 7/1997 | Burk | |
| 5,654,011 A | 8/1997 | Jackson et al. | |
| 5,675,789 A | 10/1997 | Ishii et al. | |
| 5,686,107 A | 11/1997 | Ratnaraj et al. | |
| 5,770,215 A * | 6/1998 | Moshyedi | 424/440 |
| 5,775,652 A | 7/1998 | Crawshaw et al. | |
| 5,807,586 A | 9/1998 | Jackson et al. | |
| 5,869,084 A * | 2/1999 | Paradissis et al. | 424/439 |
| 5,879,698 A | 3/1999 | Ellenbogen et al. | |
| 5,922,361 A | 7/1999 | Bieser et al. | |
| 5,922,704 A | 7/1999 | Bland | |
| 5,935,610 A | 8/1999 | McLean | |
| 5,948,443 A * | 9/1999 | Riley et al. | 424/643 |
| 5,952,317 A | 9/1999 | Deluca et al. | |
| 5,962,030 A | 10/1999 | Fine | |
| 5,965,162 A | 10/1999 | Fuisz et al. | |
| 5,971,334 A | 10/1999 | Crawshaw et al. | |
| 5,976,568 A | 11/1999 | Riley | |
| 5,976,784 A | 11/1999 | DeLuca et al. | |
| 5,977,073 A | 11/1999 | Khaled | |
| 6,040,333 A | 3/2000 | Jackson | |
| 6,051,236 A | 4/2000 | Portman | |
| 6,060,093 A | 5/2000 | Davis et al. | |
| 6,080,431 A | 6/2000 | Andon et al. | |
| 6,080,788 A | 6/2000 | Sole et al. | |
| 6,086,915 A | 7/2000 | Zeligs et al. | |
| 6,106,874 A | 8/2000 | Liebrecht et al. | |
| 6,112,240 A | 8/2000 | Pogue et al. | |
| 6,124,268 A | 9/2000 | Ghosal | |
| 6,143,300 A | 11/2000 | Stevenot | |
| 6,150,399 A | 11/2000 | Patel et al. | |
| 6,150,411 A | 11/2000 | Stordy | |
| 6,174,857 B1 | 1/2001 | Burk | |
| 6,174,890 B1 | 1/2001 | Riga et al. | |
| 6,187,318 B1 | 2/2001 | Mitchell et al. | |
| 6,190,693 B1 | 2/2001 | Kafrissen et al. | |

(Continued)

OTHER PUBLICATIONS

Magnesium factsheet, [online] Office of dietary supplements, National institute of Health, Jan. 2005, Retrieved from the Internet URL: A http://web.archive.org/web/20050212015808/http://ods.od.nih.gov/factsheets/magnesium.asp.*

*Primary Examiner* — Jeffrey S. Lundgren
*Assistant Examiner* — Savitha Rao
(74) *Attorney, Agent, or Firm* — Maldjian Law Group LLC; John P. Maldjian, Esq.

(57) ABSTRACT

A composition for the nutritional supplementation of women and a method of administering a composition designed for the nutritional supplementation of women is described. In accordance with one embodiment of the present invention, such a composition comprises vitamin A, vitamin $B_1$, vitamin $B_2$, vitamin $B_6$, vitamin $B_{12}$, folic acid, vitamin $D_3$, vitamin C, vitamin E, niacin, copper, magnesium, zinc, and iron. In accordance with another embodiment of the present invention, a method of administering a composition designed for the nutritional supplementation of women comprises the step of administering a composition comprising vitamin A, vitamin $B_1$, vitamin $B_2$, vitamin $B_6$, vitamin $B_{12}$, folic acid, vitamin $D_3$, vitamin C, vitamin E, niacin, copper, magnesium, zinc, and iron.

12 Claims, No Drawings

U.S. PATENT DOCUMENTS

| | | | |
|---|---|---|---|
| 6,197,329 B1 | 3/2001 | Hermelin et al. | |
| 6,203,819 B1 | 3/2001 | Fine | |
| 6,210,686 B1 | 4/2001 | Bell et al. | |
| 6,228,388 B1 | 5/2001 | Paradissis et al. | |
| 6,235,322 B1 | 5/2001 | Lederman | |
| 6,238,672 B1 | 5/2001 | Chen | |
| 6,241,997 B1 | 6/2001 | Kershman et al. | |
| 6,245,378 B1 | 6/2001 | Cavazza | |
| 6,248,909 B1 | 6/2001 | Akimoto et al. | |
| 6,255,341 B1 | 7/2001 | DeMichele et al. | |
| 6,258,846 B1 | 7/2001 | Hermelin et al. | |
| 6,261,600 B1 | 7/2001 | Kirschner et al. | |
| 6,265,438 B1 | 7/2001 | Steward | |
| 6,277,396 B1 | 8/2001 | Dente | |
| 6,290,974 B1 | 9/2001 | Swaisgood et al. | |
| 6,291,517 B1 | 9/2001 | Bagchi et al. | |
| 6,291,533 B1 | 9/2001 | Fleischner | |
| 6,299,886 B1 | 10/2001 | Piper | |
| 6,299,896 B1 | 10/2001 | Cooper et al. | |
| 6,300,309 B1 | 10/2001 | Guler et al. | |
| 6,346,284 B1 | 2/2002 | Briend et al. | |
| 6,352,713 B1 | 3/2002 | Kirschner et al. | |
| 6,358,544 B1 | 3/2002 | Henry, Jr. et al. | |
| 6,358,925 B1 | 3/2002 | Guler et al. | |
| 6,361,800 B1 | 3/2002 | Cooper et al. | |
| 6,362,221 B1 | 3/2002 | Clark et al. | |
| 6,365,176 B1 | 4/2002 | Bell et al. | |
| 6,368,640 B1 | 4/2002 | Wuh et al. | |
| 6,369,042 B1 | 4/2002 | Oberthur et al. | |
| 6,372,782 B1 | 4/2002 | Patel et al. | |
| 6,410,058 B2 | 6/2002 | Gohlke et al. | |
| 6,416,737 B1 | 7/2002 | Manolagas et al. | |
| 6,420,350 B1 | 7/2002 | Fleischner | |
| 6,426,097 B2 | 7/2002 | Grose | |
| 6,432,442 B1 | 8/2002 | Buehler et al. | |
| 6,436,406 B1 | 8/2002 | Yegorova | |
| 6,436,453 B1 | 8/2002 | van Lengerich et al. | |
| 6,436,910 B1 | 8/2002 | Yerxa et al. | |
| 6,440,450 B1 | 8/2002 | Han et al. | |
| 6,444,218 B2 | 9/2002 | Han et al. | |
| 6,447,809 B1 | 9/2002 | Krumhar et al. | |
| 6,451,341 B1 | 9/2002 | Slaga et al. | |
| 6,455,068 B1 | 9/2002 | Licari | |
| 6,455,714 B1 | 9/2002 | Holick et al. | |
| 6,461,652 B1 | 10/2002 | Henry et al. | |
| 6,465,013 B1 | 10/2002 | DeBernardi | |
| 6,468,568 B1 | 10/2002 | Leusner et al. | |
| 6,475,511 B2 | 11/2002 | Gohlke et al. | |
| 6,475,539 B1 | 11/2002 | DeWille et al. | |
| 6,479,545 B1 | 11/2002 | Levinson et al. | |
| 6,485,738 B1 | 11/2002 | Huang et al. | |
| 6,488,956 B1 | 12/2002 | Paradissis et al. | |
| 6,495,173 B1 | 12/2002 | Yegorova | |
| 6,495,177 B1 * | 12/2002 | deVries et al. | 426/72 |
| 6,495,736 B1 | 12/2002 | Brunkow et al. | |
| 6,497,885 B2 | 12/2002 | Trant | |
| 6,497,906 B1 | 12/2002 | Kelly | |
| 6,503,529 B1 | 1/2003 | Fleischner | |
| 6,509,045 B2 | 1/2003 | Henry et al. | |
| 6,509,326 B1 | 1/2003 | Andon et al. | |
| 6,517,861 B2 | 2/2003 | Singh et al. | |
| 6,521,247 B1 | 2/2003 | deVries | |
| 6,541,005 B1 | 4/2003 | Yegorova | |
| 6,541,006 B1 | 4/2003 | Yegorova | |
| 6,544,525 B1 | 4/2003 | Yegorova | |
| 6,544,563 B2 | 4/2003 | Wuh et al. | |
| 6,562,378 B1 | 5/2003 | Chandra | |
| 6,565,891 B1 | 5/2003 | Chandra | |
| 6,569,445 B2 | 5/2003 | Manning et al. | |
| 6,569,477 B2 | 5/2003 | Lederman | |
| 6,569,857 B1 | 5/2003 | Hermelin et al. | |
| 6,569,869 B2 | 5/2003 | Assmann et al. | |
| 6,576,242 B1 | 6/2003 | Yegorova | |
| 6,576,253 B2 | 6/2003 | Manning et al. | |
| 6,576,666 B2 | 6/2003 | Hermelin et al. | |
| 6,579,544 B1 | 6/2003 | Rosenberg et al. | |
| 6,579,899 B1 | 6/2003 | Wurtman et al. | |
| 6,585,998 B2 | 7/2003 | Cartwright et al. | |
| 6,592,863 B2 | 7/2003 | Fuchs et al. | |
| 6,592,909 B2 | 7/2003 | Belcheff | |
| 6,593,310 B1 | 7/2003 | Cullis-Hill | |
| 6,596,313 B2 | 7/2003 | Rosenbloom | |
| 6,596,762 B2 | 7/2003 | Sokol | |
| 6,605,646 B2 | 8/2003 | Herbert | |
| 6,630,158 B2 | 10/2003 | Popp et al. | |
| 6,642,212 B1 | 11/2003 | Kelly | |
| 6,646,013 B1 | 11/2003 | Barker et al. | |
| 6,653,332 B2 | 11/2003 | Jaen et al. | |
| 6,660,293 B2 | 12/2003 | Giordano et al. | |
| 6,667,063 B2 | 12/2003 | Crum | |
| 6,706,478 B2 | 3/2004 | Duff et al. | |
| 6,720,013 B2 | 4/2004 | Johnson et al. | |
| 6,743,770 B2 | 6/2004 | Bell et al. | |
| 6,752,986 B2 | 6/2004 | Bauer et al. | |
| 6,756,401 B2 | 6/2004 | Day et al. | |
| 6,780,438 B2 | 8/2004 | Gohlke et al. | |
| 6,790,462 B2 | 9/2004 | Hendricks | |
| 6,793,935 B2 | 9/2004 | Hermelin et al. | |
| 6,797,077 B2 | 9/2004 | Pearl | |
| 6,814,983 B2 * | 11/2004 | Giordano et al. | 424/630 |
| 6,818,228 B1 | 11/2004 | Walsdorf et al. | |
| 6,818,234 B1 | 11/2004 | Nair et al. | |
| 6,827,945 B2 | 12/2004 | Rosenbloom | |
| 6,830,761 B1 | 12/2004 | Zlotkin | |
| 6,835,402 B1 | 12/2004 | Clark et al. | |
| 6,837,682 B2 | 1/2005 | Evenson et al. | |
| 6,844,012 B1 | 1/2005 | Forceville et al. | |
| 6,849,274 B1 | 2/2005 | Whittle | |
| 6,849,613 B2 | 2/2005 | Prasad et al. | |
| 6,852,335 B2 | 2/2005 | DeBernardi et al. | |
| 6,863,904 B2 | 3/2005 | Giordano et al. | |
| 6,881,419 B2 | 4/2005 | Lovett | |
| 6,881,425 B2 | 4/2005 | Pushpangadan et al. | |
| 6,887,850 B2 | 5/2005 | Fuchs et al. | |
| 6,914,073 B2 | 7/2005 | Boulos et al. | |
| 6,929,807 B1 | 8/2005 | McAnalley et al. | |
| 6,953,588 B2 | 10/2005 | Cooper et al. | |
| 6,955,873 B1 | 10/2005 | Blum | |
| 6,960,581 B2 | 11/2005 | Betageri et al. | |
| 6,995,166 B1 | 2/2006 | Giordano et al. | |
| 2001/0022980 A1 | 9/2001 | Bell et al. | |
| 2001/0031283 A1 | 10/2001 | Belcheff | |
| 2001/0031744 A1 | 10/2001 | Kosbab | |
| 2001/0036468 A1 | 11/2001 | Han et al. | |
| 2001/0036936 A1 | 11/2001 | Day et al. | |
| 2001/0041741 A1 | 11/2001 | Sole et al. | |
| 2001/0055623 A1 | 12/2001 | Jackson | |
| 2002/0015762 A1 | 2/2002 | Quinlan | |
| 2002/0032234 A1 | 3/2002 | Hermelin et al. | |
| 2002/0034543 A1 | 3/2002 | Kirschner et al. | |
| 2002/0037928 A1 | 3/2002 | Jaen et al. | |
| 2002/0044957 A1 | 4/2002 | Fuchs et al. | |
| 2002/0044961 A1 | 4/2002 | Kirschner et al. | |
| 2002/0044988 A1 | 4/2002 | Fuchs et al. | |
| 2002/0058088 A1 | 5/2002 | Henry et al. | |
| 2002/0064578 A1 | 5/2002 | Henry et al. | |
| 2002/0069197 A1 | 6/2002 | Katayama et al. | |
| 2002/0099032 A1 | 7/2002 | Higashi et al. | |
| 2002/0102330 A1 | 8/2002 | Schramm et al. | |
| 2002/0110604 A1 | 8/2002 | Babish et al. | |
| 2002/0116249 A1 | 8/2002 | Ellinger et al. | |
| 2002/0119183 A1 | 8/2002 | Hermelin et al. | |
| 2002/0119928 A1 | 8/2002 | McAnalley | |
| 2002/0119933 A1 | 8/2002 | Butler et al. | |
| 2002/0132800 A1 | 9/2002 | Popp et al. | |
| 2002/0136711 A1 | 9/2002 | Cochran | |
| 2002/0136782 A1 | 9/2002 | Fleischner | |
| 2002/0137749 A1 | 9/2002 | Levinson et al. | |
| 2002/0146471 A1 | 10/2002 | Wuh et al. | |
| 2002/0147152 A1 | 10/2002 | Bell et al. | |
| 2002/0147153 A1 | 10/2002 | Bell et al. | |
| 2002/0150607 A1 | 10/2002 | Schramm et al. | |
| 2002/0150649 A1 | 10/2002 | Bell | |
| 2002/0155163 A1 | 10/2002 | Benjamin et al. | |
| 2002/0155181 A1 | 10/2002 | Wuh et al. | |
| 2002/0168429 A1 | 11/2002 | Mann | |
| 2002/0172721 A1 | 11/2002 | Boulos et al. | |

| Publication No. | Date | Inventor |
|---|---|---|
| 2002/0173510 A1 | 11/2002 | Levinson et al. |
| 2002/0187205 A1 | 12/2002 | Paradissis et al. |
| 2002/0193379 A1 | 12/2002 | Copp et al. |
| 2002/0197330 A1 | 12/2002 | Jackson et al. |
| 2003/0012824 A1 | 1/2003 | Ott et al. |
| 2003/0012826 A1 | 1/2003 | Giordano et al. |
| 2003/0013639 A1 | 1/2003 | Yurchak et al. |
| 2003/0017205 A1 | 1/2003 | DeBernardi |
| 2003/0031726 A1 | 2/2003 | Hendricks |
| 2003/0044473 A1 | 3/2003 | Fleischner |
| 2003/0059481 A1 | 3/2003 | Krumhar et al. |
| 2003/0068372 A1 | 4/2003 | Kirschner et al. |
| 2003/0091552 A1 | 5/2003 | Cartwright et al. |
| 2003/0091613 A1 | 5/2003 | DeWille et al. |
| 2003/0096018 A1 | 5/2003 | Schloss et al. |
| 2003/0099730 A1 | 5/2003 | Rosenbloom |
| 2003/0104078 A1 | 6/2003 | Barrett-Reis et al. |
| 2003/0108594 A1 | 6/2003 | Manning et al. |
| 2003/0108605 A1 | 6/2003 | Hermelin et al. |
| 2003/0108624 A1 | 6/2003 | Kosbab |
| 2003/0138484 A1 | 7/2003 | Gianesello et al. |
| 2003/0143287 A1 | 7/2003 | Bell |
| 2003/0147996 A1 | 8/2003 | Prasad et al. |
| 2003/0148946 A1 | 8/2003 | Levy et al. |
| 2003/0149765 A1 | 8/2003 | Hubbard et al. |
| 2003/0162807 A1 | 8/2003 | Day et al. |
| 2003/0166247 A1 | 9/2003 | Brunkow et al. |
| 2003/0170327 A1 | 9/2003 | Dahl |
| 2003/0185918 A1 | 10/2003 | Rosenbloom |
| 2003/0190355 A1 | 10/2003 | Hermelin et al. |
| 2003/0190369 A1 | 10/2003 | Lovett |
| 2003/0198661 A1 | 10/2003 | Harper et al. |
| 2003/0198730 A1 | 10/2003 | Stewart |
| 2003/0202992 A1 | 10/2003 | Fuchs et al. |
| 2003/0203053 A1 | 10/2003 | Wuh et al. |
| 2003/0206969 A1 | 11/2003 | Nidamarty et al. |
| 2003/0216351 A1 | 11/2003 | Hermelin et al. |
| 2003/0229014 A1 | 12/2003 | Schneider et al. |
| 2004/0009535 A1 | 1/2004 | Brunkow et al. |
| 2004/0013743 A1 | 1/2004 | Jackson |
| 2004/0039504 A1 | 2/2004 | Coffee et al. |
| 2004/0047898 A1 | 3/2004 | Harper et al. |
| 2004/0048812 A1 | 3/2004 | Kelly |
| 2004/0048870 A1 | 3/2004 | Amir et al. |
| 2004/0052918 A1 | 3/2004 | Briend et al. |
| 2004/0058321 A1 | 3/2004 | Brunkow et al. |
| 2004/0076664 A1 | 4/2004 | Bonura |
| 2004/0082536 A1 | 4/2004 | Cooper et al. |
| 2004/0086574 A1 | 5/2004 | Giordano et al. |
| 2004/0087515 A1 | 5/2004 | Butler et al. |
| 2004/0101554 A1 | 5/2004 | Kirschner et al. |
| 2004/0106561 A1 | 6/2004 | Kelly |
| 2004/0109901 A1 | 6/2004 | Giordano et al. |
| 2004/0162292 A1 | 8/2004 | Evenstad et al. |
| 2004/0166175 A1 | 8/2004 | Giordano et al. |
| 2004/0170702 A1 | 9/2004 | VanStockum |
| 2004/0175415 A1 | 9/2004 | Chan et al. |
| 2004/0185119 A1 | 9/2004 | Theuer |
| 2004/0191296 A1 | 9/2004 | Sternberg |
| 2004/0197430 A1 | 10/2004 | Meyrowitz |
| 2004/0198674 A1 | 10/2004 | Levy et al. |
| 2004/0209848 A1 | 10/2004 | Maruyama et al. |
| 2004/0213857 A1 | 10/2004 | Soldati et al. |
| 2004/0213873 A1 | 10/2004 | Parvez |
| 2004/0219235 A1 | 11/2004 | Pushpangadan et al. |
| 2004/0220118 A1 | 11/2004 | Bland et al. |
| 2004/0224032 A1 | 11/2004 | Zlotkin |
| 2004/0228931 A1 | 11/2004 | Chokshi et al. |
| 2004/0234544 A1 | 11/2004 | Jager et al. |
| 2004/0234579 A1 | 11/2004 | Finke |
| 2004/0235728 A1 | 11/2004 | Stoch et al. |
| 2004/0254095 A1 | 12/2004 | Martin et al. |
| 2004/0259886 A1 | 12/2004 | Day et al. |
| 2005/0009835 A1 | 1/2005 | Thomas |
| 2005/0026223 A1 | 2/2005 | Manolagas et al. |
| 2005/0032741 A1 | 2/2005 | Venkataraman |
| 2005/0037065 A1 | 2/2005 | Kirschner et al. |
| 2005/0058671 A1 | 3/2005 | Bedding et al. |
| 2005/0059641 A1 | 3/2005 | Ray et al. |
| 2005/0069608 A1 | 3/2005 | Hendricks |
| 2005/0095262 A1 | 5/2005 | Camponovo et al. |
| 2005/0100613 A1 | 5/2005 | Giordano et al. |
| 2005/0101670 A1 | 5/2005 | Hermelin et al. |
| 2005/0106266 A1 | 5/2005 | Levinson et al. |
| 2005/0112176 A1 | 5/2005 | Dopson et al. |
| 2005/0112177 A1 | 5/2005 | Dopson et al. |
| 2005/0112211 A1 | 5/2005 | Gervais et al. |
| 2005/0119218 A1 | 6/2005 | Prasad et al. |
| 2005/0123628 A1 | 6/2005 | Zabrecky |
| 2005/0130933 A1 | 6/2005 | Jacobs et al. |
| 2005/0142124 A1 | 6/2005 | Kaiser |
| 2005/0143357 A1 | 6/2005 | Pousette et al. |
| 2005/0153019 A1 | 7/2005 | Fuchs et al. |
| 2005/0171034 A1 | 8/2005 | Halevie-Goldman |
| 2005/0186252 A1 | 8/2005 | Ahlgren et al. |
| 2005/0187144 A1 | 8/2005 | Fine et al. |
| 2005/0196343 A1 | 9/2005 | Reddy et al. |
| 2005/0196434 A1 | 9/2005 | Brierre |
| 2005/0196469 A1 | 9/2005 | Thys-Jacobs |
| 2005/0198239 A1 | 9/2005 | Hughes |
| 2005/0214383 A1 | 9/2005 | Bubnis et al. |
| 2005/0214388 A1 | 9/2005 | Gorham et al. |
| 2005/0226942 A1 | 10/2005 | Myhill et al. |
| 2005/0233946 A1 | 10/2005 | Fine et al. |
| 2005/0233947 A1 | 10/2005 | Fine et al. |
| 2005/0249787 A1 | 11/2005 | Reynolds et al. |
| 2005/0249788 A1 | 11/2005 | Reynolds et al. |
| 2005/0256178 A1 | 11/2005 | Eggersdorfer et al. |
| 2005/0260284 A1 | 11/2005 | DiMateeo-Leggio |
| 2005/0261172 A1 | 11/2005 | Schneider et al. |
| 2005/0261257 A1 | 11/2005 | Vermeer |
| 2005/0281888 A1 | 12/2005 | Chandra |
| 2005/0281889 A1 | 12/2005 | Chandra |
| 2005/0282794 A1 | 12/2005 | Fine et al. |
| 2005/0286646 A1 | 12/2005 | Fails et al. |
| 2005/0287228 A1 | 12/2005 | Trant |
| 2005/0289279 A1 | 12/2005 | Fails et al. |
| 2005/0289379 A1 | 12/2005 | Teutsch et al. |
| 2006/0003981 A1 | 1/2006 | Fine et al. |
| 2006/0008543 A1 | 1/2006 | Myhill et al. |
| 2006/0008544 A1 | 1/2006 | Myhill et al. |
| 2006/0018975 A1 | 1/2006 | Talbott |
| 2006/0024384 A1 | 2/2006 | Giordano |
| 2006/0024409 A1 | 2/2006 | Giordano |
| 2006/0034912 A1 | 2/2006 | Giordano et al. |
| 2006/0034916 A1 | 2/2006 | Giordano et al. |

* cited by examiner

NUTRITIONAL SUPPLEMENT FOR WOMEN

BACKGROUND OF THE INVENTION

1. Field of the Invention

Embodiments of the present invention generally relate to nutritional supplements and in particular to nutritional supplements for use by women.

2. Description of the Related Art

Nutrition plays a critical role in maintaining good health, especially in women during child bearing years. Prescription multi-vitamins/multi-mineral nutritional supplements are often needed for improving the nutritional status of women prior to conception, throughout pregnancy and in the post natal period for both lactating and non-lactating mothers. Pregnancy and lactation are among the most nutritionally volatile and physiologically stressful periods in processes in the lifetime of a woman.

Specifically, vitamin and mineral needs are almost universally increased during these natural processes. These increased needs are almost always due to elevated metabolic demand, increased plasma volume, increased levels of blood cells, decreased concentrations of nutrients, and decreased concentrations of nutrient-binding proteins.

Research has suggested that optimizing specific nutrients before, during and after physiological processes of pregnancy and lactation can have a profound, positive and comprehensive impact upon the overall wellness of the mother and of the developing and newborn child, as well as, the safety and health of the mother.

Thus, there is a need for a nutritional supplement to be used in improving the nutritional status of women prior to conception, throughout pregnancy and in the post natal period for both lactating and non-lactating mothers.

SUMMARY OF THE INVENTION

The present invention relates to nutritional supplements for women during pre-pregnancy and post-pregnancy in both lactating and non-lactating conditions. The nutritional supplement comprises a source of vitamin A, a source of vitamin B1, a source of vitamin B2, a source of vitamin B6, a source of vitamin B12, folic acid, vitamin D3, vitamin C, vitamin E and niacin, and a source of minerals including copper, magnesium, zinc and iron.

The nutritional supplement can be made in a variety of forms, such as the following pharmaceutical compositions: a pill, a tablet, a caplet, a capsule, a chewable tablet, a quick dissolve tablet, an effervescent tablet, a hard gelatin capsule, a soft gelatin capsule, a powder, a liquid suspension, and a food product. One skilled in the art would recognize there are also other viable ways for delivering the nutritional supplement to a user.

DETAILED DESCRIPTION

It is understood that the embodiments of the present invention are not limited to the particular methodologies, protocols, solvents and reagents, and the like, described herein as they may vary. It is also to be understood the terminology used herein is used for the purpose of describing particular embodiments only and not intended to limit the scope of the present invention. It must also be noted that as used herein and in the appended claims, the singular form "a," "an" and "the" include the plural reference unless the context clearly dictates otherwise. Thus, for example, a reference to "a vitamin" is a reference to one or more vitamins and includes equivalents thereof know to those skilled in the art and so forth.

Unless defined otherwise, all technical and scientific terms used herein have the same meaning as commonly understood by one of ordinary skilled in the art to which this invention belongs. Preferred methods, devices and materials are described, although any methods and materials similar or equivalent to those described herein could be used in the practice or testing of the present invention. All references cited herein are incorporated by reference herein in there entirety.

The term "disease state" as used herein, may comprise any state in which one or more organs or components of an organism malfunction. The term includes "disease state" may refer to any deterioration of any component of a body. The term "disease state" may refer to any deficiency of any compound necessary for the maintenance or function of any component of any organism. The term "disease state" may refer to any condition in which a body contains toxins, produced by microorganisms that infect the body or by body cells through faulty metabolism or absorbed from an external source.

The term "disease states" may be adverse states caused by any diet, any virus, or any bacteria. "Disease states" may comprise disorders associated with pregnant females such as for example, osteomalacia and preeclampsia and disorders associated with a fetus such as, for example, neurotube defects and various fetal abnormalities. "Disease states" may comprise any pulmonary disorder such as, for example, bronchitis, bronchiectasis, atelectasis, pneumonia, diseases caused by inorganic dust, diseases caused by organic dust, any pulmonary fibrosis, and pleurisy. "Disease states" may comprise any hematological/oncological disorders such as, for example, anemia, hemophilia, leukemia, lymphoma.

A "disease state" may comprise any cancer such as, for example, breast cancer, lung cancer, prostate cancer, pancreatic cancer, liver cancer, stomach cancer, testicular cancer, ovarian cancer, skin cancer, cancer of the brain, cancer of the mouth, cancer of the throat, and cancer of the neck. "Disease states" may comprise any disorder of the immune system such as, for example, Acquired Immune Deficiency Syndrome (AIDS), AIDS-related complex, infection by any strain of any Human Immunodeficiency Virus (HIV), and other viruses and pathogens such as bacteria.

A "disease state" may comprise any cardiovascular disorders such as, for example, arterial hypertension, orthostatic hypotension, arteriolosclerosis, coronary artery disease, cardiomyopathy, any arrhythmia, any valvular heart disease, endocarditis, pericardial disease, any cardiac tumor, any aneurism, and any peripheral vascular disorder. "Disease states" may comprise any hepatic/biliary disorders such as, for example, jaundice, hepatic steatosis, fibrosis, cirrhosis, hepatitis, any hepatic granuloma, any liver tumor, cholelithiasis, cholecystitis, and choledocholithiasis.

The term "physiologically stressful state," as used herein, comprises any state of an organism in which the organism faces one or more physiological challenges. A "physiologically stressful state" may comprise pre-pregnancy, pregnancy, lactation, or conditions in which an organism faces physiological challenges related to for example, elevated metabolic demand, increased plasma volume, or decreased concentrations of nutrient-binding proteins. A "physiologically stressful state" may result from one or more disease states.

The term "subject" as used herein comprises any and all organisms and includes the term "patient." "Subject" may refer to a human or any other animal. "Subject" may also refer to a fetus.

Proper nutrition is essential for maintaining health and preventing diseases. Adequate nutrition is especially critical during for example, nutritionally volatile or physiologically stressful. Such as periods comprising for example, pre-pregnancy, pregnancy, lactation, or a disease state. Vitamin and mineral needs are almost universally increased throughout these periods. Increased needs during physiologically stressful states such as pre-pregnancy, pregnancy, or lactation, for example, may result from elevated metabolic demand, increased plasma volume, increased quantities of circulating red blood cells, decreased concentrations of nutrients, and decreased concentrations of nutrient-binding protein such as, serum ferritin, maltose-binding protein, lactoferrin, calmodulin, tocopheryl binding protein, riboflavin binding protein, retinal binding protein, transferritin high density lipoprotein-apolipoprotein A1, folic acid binding protein, and 25-hydrooxy vitamin D binding protein.

In one embodiment, the nutritional supplement comprises about 2,100 IUs of vitamin A, about 2 mg of vitamin B1, about 3.4 mg of vitamin B2, about 10 mg of vitamin B6, about 15 mcg of vitamin B12, about 1.25 mg of folic acid, about 315 IUs of vitamin D3, about 120 mg vitamin C, about 20 IUs of vitamin E, about 10 mg of niacin, about 1 mg of copper, about 15 mg of magnesium, about 10 mg of zinc and about 50 mg of iron.

In another embodiment the inactive ingredients include croscarmellosesodium, microcrystalline cellulose, calcium phosphate, stearic acid, magnesium stearate, silica, povidone, hydroxypropyl methylcellulose, titanium dioxide, FD&C red number 40.

The nutritional supplement can be made in a variety of forms, such as pharmaceutical compositions (e.g., tablet, powder, suspension, liquid, capsule, and gel), nutritional beverages, puddings, confections (e.g., candy), ice cream, frozen confections and novelties or non-baked, extruded food products such as bars.

In another embodiment, the ingredients of the nutritional supplement can be administered separately, just by incorporating certain components (e.g., bitter tasting ones) into a capsule or tablet and the remaining ingredients provided as a powder or nutritional bar. A preferred form of nutritional supplement is a multi-vitamin/mineral with iron tablet specially formulated for women pre-pregnancy, during pregnancy and post-pregnancy. The nutritional supplement can be formulated for single or multiple daily administration, preferably one bisected tablet daily or as prescribed by a physician.

The embodiments of the present invention further pertain to therapeutic methods for managing nutrition of women during pre-pregnancy, pregnancy and post-pregnancy. The nutritional supplement can be administered to a woman to mitigate reduced amounts of nutrition and increase the healthiness of an unborn and a newborn.

Vitamin A is a family of fat-soluble compounds that play an important role in vision, bone growth, reproduction, cell division, and cell differentiation (in which a cell becomes part of the brain, muscle, lungs, etc.). Vitamin A helps regulate the immune system, which helps prevent or fight off infections by making white blood cells that destroy harmful bacteria and viruses. Vitamin A also may help lymphocytes, a type of white blood cell, fight infections more effectively. Vitamin A promotes healthy surface linings of the eyes and the respiratory, urinary, and intestinal tracts. When those linings break down, it becomes easier for bacteria to enter the body and cause infection. Vitamin A also helps maintain the integrity of skin and mucous membranes, which also function as a barrier to bacteria and viruses.

Vitamin E, a fat-soluble vitamin, is an antioxidant vitamin involved in the metabolism of all cells. It protects vitamin A and essential fatty acids from oxidation in the body cells and prevents breakdown of body tissues.

Vitamin D3 is a naturally occurring bodily substance that many believe exert a protective effect in multiple sclerosis—both in the development of the disease and in limiting its progression. It is naturally produced in the skin in response to sunlight but is also present in certain foodstuffs (particularly oily fish). Vitamin D3 is a type of steroid hormone and among other things, a powerful mediator of immune function.

Vitamin D3 is best known for it's effects on calcium metabolism. Proper levels are necessary to maintain bone mineral density and serum (blood) calcium levels. This is especially true among the very young where it is used to treat rickets and in combination with vitamin A for the treatment of osteoporosis in the elderly, particularly post menopausal women who are often subject to fractures due to loss of bone density.

In studies, Vitamin D3 has been found helpful against autoimmunity for the down-regulation of Th1 and up-regulation of Th2 cells. It has also been shown to regulate the neurotrophins NGF (Nerve Growth Factor), NT-3 (NeuroTrophin 3) and NT-4. In addition, Vitamin D3 has also been found to promote differentiation and cell death in neuroblastoma (brain tumor) cell lines as well as cancers in general.

Vitamin C is a water-soluble, antioxidant vitamin. It is important in forming collagen, a protein that gives structure to bones, cartilage, muscle, and blood vessels. Vitamin C also aids in the absorption of iron, and helps maintain capillaries, bones, and teeth. As a water-soluble antioxidant, vitamin C is in a unique position to "scavenge" aqueous peroxyl radicals before these destructive substances have a chance to damage lipids. It works along with vitamin E, a fat-soluble antioxidant, and the enzyme glutathione peroxidase to stop free radical chain reactions. Vitamin C can enhance the body's resistance to an assortment of diseases, including infectious disorders and many types of cancer. It strengthens and protects the immune system by stimulating the activity of antibodies and immune system cells such as phagocytes and neutrophils. Vitamin C contributes to a variety of other biochemical functions. These include the biosynthesis of the amino acid carnitine and the catecholamines that regulate the nervous system. It also helps the body to absorb iron and to break down histamine. Although vitamin C is found in every cell, it is especially useful in key parts of the body. These include the blood, the skin, the nervous system, the teeth and bones and glands such as the thymus, adrenals and thyroid.

Vitamin B1, also known as thiamin, helps fuel your body by converting blood sugar into energy. It keeps the mucous membranes healthy and is essential for nervous system, cardiovascular and muscular function. Vitamin B1 (thiamin) is essential for the metabolism of carbohydrates to produce energy and for normal nerve and heart function.

Niacin, vitamin B3 is required for cell respiration, helps in the release of energy and metabolism of carbohydrates, fats, and proteins, proper circulation and healthy skin, functioning of the nervous system, and normal secretion of bile and stomach fluids. It is used in the synthesis of sex hormones, treating schizophrenia and other mental illnesses, and a memory-enhancer. Niacin given in pharmaceutical dosage improves the blood cholesterol profile, and has been used to clear the body of organic poisons, such as certain insecticides.

Folic acid is a water-soluble vitamin in the B-complex group. Folic acid works along with vitamin B12 and vitamin C to help the body digest and utilize proteins and to synthesize new proteins when they are needed. It is necessary for the production of red blood cells and for the synthesis of DNA. Folic acid also helps with tissue growth and cell function. In addition, it helps to increase appetite when needed and stimulates the formation of digestive acids. Folic acid supplements may be used in the treatment of disorders associated with folic acid deficiency and may also be part of the recommended treatment for certain menstrual problems and leg ulcers.

Vitamin B6 is a water-soluble vitamin that exists in three major chemical forms: pyridoxine, pyridoxal, and pyridoxamine. It performs a wide variety of functions in the body and is essential for good health. For example, vitamin B6 is needed for more than 100 enzymes involved in protein metabolism. It is also essential for red blood cell metabolism. The nervous and immune systems need vitamin B6 to function efficiently, and it is also needed for the conversion of tryptophan to niacin.

The body needs vitamin B6 to make hemoglobin. Hemoglobin within red blood cells carries oxygen to tissues. Vitamin B6 also helps increase the amount of oxygen carried by hemoglobin. A vitamin B6 deficiency can result in a form of anemia that is similar to iron deficiency anemia.

Vitamin B6 also helps maintain your blood glucose (sugar) within a normal range. When caloric intake is low your body needs vitamin B6 to help convert stored carbohydrate or other nutrients to glucose to maintain normal blood sugar levels.

Vitamin B12, a water-soluble vitamin, is also called cobalamin because it contains the metal cobalt. This vitamin helps maintain healthy nerve cells and red blood cells. It is also needed to help make DNA, the genetic material in all cells.

Magnesium is the fourth most abundant mineral in the body, and is essential to good health. Approximately 50% of total body magnesium is found in the bone. The other half is found predominantly inside cells of body tissues and organs. Only 1% of magnesium is found in blood, but the body works very hard to keep blood levels of magnesium constant. Magnesium is needed for more than 300 biochemical reactions in the body. It helps maintain normal muscle and nerve function, keeps heart rhythm steady, supports a healthy immune system, and keeps bones strong. Magnesium also helps regulate blood sugar levels, promotes normal blood pressure, and is known to be involved in energy metabolism and protein synthesis. Magnesium may play a role in preventing and managing disorders such as hypertension, cardiovascular disease, and diabetes.

Zinc is vital for the healthy working of many of the body's systems. Zinc plays a crucial role in growth and cell division where it is required for protein and DNA synthesis, in insulin activity, in the metabolism of the ovaries and testes, and in liver function. As a component of many enzymes, zinc is involved in the metabolism of proteins, carbohydrates, lipids and energy. Zinc helps with the healing of wounds and is a vital component of many enzyme reactions. It is also important for healthy skin and is essential for a healthy immune system and resistance to infection.

Iron is an essential nutrient that carries oxygen and forms part of the oxygen-carrying proteins, hemoglobin in red blood cells and myoglobin in muscle. Iron is also a structural component at the catalytic site of a large number of enzymes covering a wide array of diverse metabolic functions. These include neurotransmitter synthesis and function, phagocyte antimicrobial activity, hepatic detoxification systems, and synthesis of DNA, collagen and bile acids.

Copper is needed for normal growth and health. Copper is also needed to help the body use iron. It is also important for nerve function, bone growth, and to help the body use sugar.

While the foregoing is directed to embodiments of the present invention, other and further embodiments of the invention may be devised without departing from the basic scope thereof, and the scope thereof is determined by the claims that follow.

What is claimed is:

1. A dosing formulation for a composition, the dosing formulation comprising a single dosage formulation of the composition, wherein the composition consists of:

about 2100 IUs to about 4200 IUs of vitamin A, about 2 mg to about 4 mg of vitamin B1, about 3.4 mg to about 6.8 mg of vitamin B2, about 10 mg to about 20 mg of vitamin B6, about 15 mcg to about 30 mcg of vitamin B12, about 1.25 mg to about 2.5 mg of folic acid, about 310 IUs to about 630 IUs of vitamin D3, about 120 mg to about 240 mg of vitamin C, about 20 IUs to about 40 IUs of vitamin E, about 10 mg to about 20 mg of niacin, about 1 mg to about 2 mg of copper, about 15 mg to about 30 mg of magnesium, about 10 mg to about 20 mg of zinc and about 50 mg to about 100 mg of iron.

2. A dosing formulation of a composition, the dosing formulation comprising a single dose formulation of the composition, wherein the composition consists of:

about 2,100 IUs of vitamin A, about 2 mg of vitamin B1, about 3.4 mg of vitamin B2, about 10 mg of vitamin B6, about 15 mcg of vitamin B12, about 1.25 mg of folic acid, about 315 IUs of vitamin D3, about 120 mg of vitamin C, about 20 IUs of vitamin E, about 10 mg of niacin, about 1 mg of copper, about 15 mg of magnesium, about 10 mg of zinc and about 50 mg of iron.

3. The dosing formulation of claim 1, wherein the single dosage formulation is selected from the group consisting of a pill, a tablet, a caplet, a capsule, a chewable tablet, a quick dissolve tablet, a powder, an effervescent tablet, a hard gelatin capsule, and a soft gelatin capsule.

4. The dosing formulation of claim 3, wherein the single dosage formulation comprises an enteric coating.

5. The dosing formulation of claim 2, wherein the single dosage formulation is selected from the group consisting of a pill, a tablet, a caplet, a capsule, a chewable tablet, a quick dissolve tablet, a powder, an effervescent tablet, a hard gelatin capsule, and a soft gelatin capsule.

6. The dosing formulation of claim 5, wherein the single dosage formulation comprises an enteric coating.

7. The dosing formulation of claim 1, wherein the single dosage formulation comprises a liquid suspension.

8. The dosing formulation of claim 1, wherein the single dosage formulation comprises a food product.

9. The dosing formulation of claim 2, wherein the single dosage formulation comprises a liquid suspension.

10. The dosing formulation of claim 2, wherein the single dosage formulation comprises a food product.

11. A method, comprising the step of administering to an individual a composition consisting of about 2100 IUs to about 4200 IUs of vitamin A, about 2 mg to about 4 mg of vitamin B1, about 3.4 mg to about 6.8 mg of vitamin B2, about 10 mg to about 20 mg of vitamin B6, about 15 mcg to about 30 mcg of vitamin B12, about 1.25 mg to about 2.5 mg of folic acid, about 310 IUs to about 630 IUs of vitamin D3, about 120 mg to about 240 mg of vitamin C, about 20 IUs to about 40 IUs of vitamin E, about 10 mg to about 20 mg of niacin, about 1 mg to about 2 mg of copper, about 15 mg to about 30 mg of magnesium, about 10 mg to about 20 mg of zinc and about 50 mg to about 100 mg of iron.

12. A method, comprising the step of administering to an individual a composition consisting of about 2,100 IUs of vitamin A, about 2 mg of vitamin B1, about 3.4 mg of vitamin B2, about 10 mg of vitamin B6, about 15 mcg of vitamin B12, about 1.25 mg of folic acid, about 315 IUs of vitamin D3, about 120 mg of vitamin C, about 20 IUs of vitamin E, about 10 mg of niacin, about 1 mg of copper, about 15 mg of magnesium, about 10 mg of zinc and about 50 mg of iron.

* * * * *